US00PP18019P2

(12) United States Plant Patent
Klemm

(10) Patent No.: US PP18,019 P2
(45) Date of Patent: Sep. 11, 2007

(54) ***GERANIUM* PLANT NAMED 'KLEP04116'**

(50) Latin Name: *Pelargonium peltatum*
Varietal Denomination: KLEP04116

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/349,716

(22) Filed: Feb. 7, 2006

(51) Int. Cl.
*A01H 5/00* (2006.01)

(52) U.S. Cl. ..... Plt./322
(58) Field of Classification Search ..... Plt./332
See application file for complete search history.

(56) References Cited

U.S. PATENT DOCUMENTS

PP10,380 P * 5/1998 Hanes ..... Plt./332
PP12,448 P2 * 3/2002 Hanes ..... Plt./332

OTHER PUBLICATIONS

UPOV ROM GTITM Computer Database, GTI Jouve Retrieval Software 2006/05, Citations for 'KLEP04116'.*

* cited by examiner

*Primary Examiner*—Wendy Haas
(74) *Attorney, Agent, or Firm*—C. A. Whealy

(57) ABSTRACT

A new and distinct cultivar of Ivy *Geranium* plant named 'KLEP04116', characterized by its outwardly spreading to trailing growth habit; freely branching habit; early and freely flowering habit; dark pink purple-colored double flowers arranged in umbels; and good garden performance.

1 Drawing Sheet

Botanical designation: *Pelargonium peltatum.*
Cultivar denomination: 'KLEP04116'.

BACKGROUND OF THE INVENTION

The present invention relates to a new and distinct cultivar of *Geranium* plant, botanically known as *Pelargonium peltatum,* and hereinafter referred to by the name 'KLEP04116'.

The new Ivy *Geranium* is a product of a planned breeding program conducted by the Inventor in Stuttgart, Germany. The objective of the breeding program was to develop new freely branching Ivy *Geraniums* with uniform and trailing plant habit and interesting flower and foliage colors.

The new Ivy *Geranium* originated from a cross-pollination made by the Inventor in July, 2000 of a proprietary selection of *Pelargonium peltatum* identified as code number GU 014, not patented, as the female, not patented, as the male, or pollen parent. The cultivar now abandoned, as the male, or pollen, parent. The cultivar KLEP04116 was discovered and selected by the Inventor as a flowering plant within the resulting progeny from this cross-pollination in a controlled environment in Stuttgart, Germany, in June, 2001.

Asexual reproduction of the new cultivar by terminal cuttings taken in a controlled environment in Stuttgart, Germany since 2001 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'KLEP04116'. These characteristics in combination distinguish 'KLEP04116' as a new cultivar and distinguish it from other known Ivy *Geranium* cultivars:

1. Outwardly spreading to trailing growth habit.
2. Freely branching habit.
3. Early and freely flowering habit.
4. Dark pink purple-colored double flowers arranged in umbels.
5. Good garden performance.

Compared to plants of the female parent selection, plants of the new Ivy *Geranium* are more freely branching. Plants of the new Ivy *Geranium* and the male parent, the cultivar Pacifique, differ primarily in plant shape as plants of the new Ivy *Geranium* are more freely branching and more uniform than plants of the cultivar Pacifique.

Plants of the new Ivy *Geranium* can be compared to plants of the cultivar Klerobright, not patented. In side-by-side comparisons conducted in Stuttgart, Germany, plants of the new Ivy *Geranium* differed from plants of the cultivar Klerobright in the following characteristics:

1. Plants of the new Ivy *Geranium* were not as vigorous as plants of the cultivar Klerobright.
2. Plants of the new Ivy *Geranium* and the cultivar Klerobright differed in flower color as plants of the cultivar Klerobright had bright red-colored flowers.
3. Plants of the new Ivy *Geranium* flowered earlier than plants of the cultivar Klerobright.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description, which accurately describe the colors of the new Ivy *Geranium*. The photograph comprises a side prespective view of a typical flowering plant of 'KLEP04116' grown in a container.

DETAILED BOTANICAL DESCRIPTION

Plants of the cultivar KLEP04116 have not been observed under all possible environmental conditions. The phenotype may vary somewhat with variations in environment, such as temperature and light intensity, without, however, any variance in genotype.

The aforementioned photograph, following observations, and averaged measurements describe plants that were planted in January in Stuttgart, Germany, and grown under commercial practice in a glass-covered greenhouse with day temperatures ranging from 16° C. to 22° C., night temperatures ranging from 12° C. to 16° C. and light levels ranging from 25,000 to 60,000 lux. Plants were pinched once during the growing period. The photograph and botanical description were taken about 13 weeks after planting rooted young plants. In the following description, color references are made to The Royal Horticultural Society Colour Chart, 1995 Edition, except where general terms of ordinary dictionary significance are used.

Botanical classification: *Pelargonium peltatum* cultivar KLEP04116.

Parentage:

*Female parent.*—Proprietary selection of *Pelargonium peltatum* identified as code number GU 014, not patented.

*Male parent.*—*Pelargonium peltatum* cultivar Pacifique, not patented.

Propagation:

*Type cutting.*—Terminal vegetative cuttings.

*Time to initiate roots, summer.*—About 8 days at 22° C.

*Time to initiate roots, winter.*—About 9 days at 20° C.

*Time to produce a rooted young plant, summer.*—About 16 days at 22° C.

*Time to produce a rooted young plant, winter.*—About 18 days at 20° C.

*Root description.*—Fine to thick, fibrous; white in color.

*Rooting habit.*—Freely branching; moderately dense.

Plant description:

*General appearance.*—Outwardly spreading to trailing plant habit; uniform; densely foliated.

*Growth and branching habit.*—Moderately vigorous. Freely branching, about five lateral branches per plant.

*Plant height* (*to top of flower umbels*).—About 27 cm to 31 cm.

*Plant height* (*to top of foliar plane*).—About 20 cm to 26 cm.

*Plant width.*—About 24 cm to 27 cm.

*Lateral branches.*—Length: About 4 cm to 5 cm. Internode length: about 1 cm to 2 cm. Texture: Smooth, glabrous. Color: 138B.

*Foliage description.*—Arrangement: Alternate, simple. Length: About 5 cm. Width: About 6 cm to 7 cm. Shape: Reniform with lobation. Apex: Rounded. Base: Peltate. Margin: Entire, lobed. Venation pattern: Palmate. Texture, upper and lower surfaces: Rough; glabrous. Color: Developing and fully expanded foliage, upper surface: 137B; venation, 137C. Developing and fully expanded foliage, lower surface: 137C; venation, 138C. Zonation pattern: Distance from margin to outer edge of zone: About 2 cm. Width: About 5 mm. Zone color: 165A. Petiole: Length: About 3.5 cm. Diameter: About 2 mm to 3 mm. Color: 138C.

Flower description:

*Flower arrangement.*—Dark pink-colored flowers arranged in rounded hemispherical umbels arising from apical leaf axils. Umbels displayed above the foliage on upright peduncles. Flowers double, rounded and cupped. Umbels persistent, flowers not persistent. Flowers not fragrant.

*Quantity of flowers.*—Freely flowering habit; at full flower, plants have at about nine developing and open umbels each with about 14 flower buds and open flowers per umbel.

*Flowering season.*—Year-round under greenhouse conditions. In the garden, flowering is continuous throughout the summer in Germany.

*Time to flower.*—Early flowering; plants start flowering about 84 days after planting rooted young plants.

*Flower longevity.*—Flowers last about four to five days on the plant.

*Umbel size.*—Height: About 6 cm to 7 cm. Diameter: About 8 cm to 9 cm.

*Flower size.*—Diameter: About 4 cm to 5 cm. Depth (height): About 2 cm.

*Flower buds.*—Length: About 6 mm to 12 mm. Diameter: About 5 mm to 8 mm. Shape: Elliptical. Color: 143B.

*Petals.*—Quantity per flower: About nine to twelve. Length: About 2.5 cm. Width: About 1.2 cm. Shape: Ovate to elliptic. Apex: Rounded. Base: Attenuate. Margin: Entire. Texture, upper and lower surfaces: Smooth, glabrous; velvety. Color: When opening and fully opened, upper surface: 81C; towards the base, 57C; venation, 57C; color does not fade with development. When opening and fully opened, lower surface: 75C; venation, 57C.

*Petaloids.*—Quantity per flower: About one to about four. Length: About 2 mm to 8 mm; irregular in size. Width: About 2 mm to 4 mm; irregular in size. Shape: Variable, irregular. Apex: Mostly rounded. Base: Attenuate. Margin: Mostly entire. Texture, upper and lower surfaces: Smooth, glabrous; velvety. Color: When opening and fully opened, upper surface: 81C; towards the base, 57C; venation, 57C; color does not fade with development. When opening and fully opened, lower surface: 75C; venation, 57C.

*Sepals.*—Quantity per flower: Five, arranged in a single whorl. Length: About 8 mm to 11 mm. Width: About 3 mm to 6 mm. Shape: Elliptical. Apex: Acute. Margin: Entire. Texture, upper and lower surfaces: Pubescent. Color, upper surface: 143B. Color, lower surface: 143C.

*Peduncle* (*umbel stem*).—Length: About 13 cm. Diameter: About 3 mm. Angle: Erect. Strength: Moderate to strong. Texture: Smooth, glabrous. Color: 143B.

*Pedicel* (*individual flower stem*).—Length: About 1.5 cm to 2.5 cm. Diameter: About 3 mm. Angle: Erect. Strength: Strong. Texture: Smooth, glabrous. Color: 143B overlain with 173A.

*Reproductive organs.*—Androecium: Anther quantity per flower: Five. Anther length: About 1.5 mm. Anther shape: Ovate. Anther color: 87D. Pollen amount: Moderate. Pollen color: 32A. Gynoecium: Pistil quantity per flower: One. Pistil length: About 5 mm. Stigma shape: Five-parted, star-shaped. Stigma color: 57C. Style length: About 4 mm. Style color: 57D. Ovary color: 149D. Seed/fruit: Seed and fruit production has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to have good garden performance and to tolerate rain, wind, and temperatures from about 8° C. to about 32° C.

It is claimed:

1. A new and distinct cultivar of Ivy *Geranium* plant named 'KLEP04116', as herein illustrated and described.

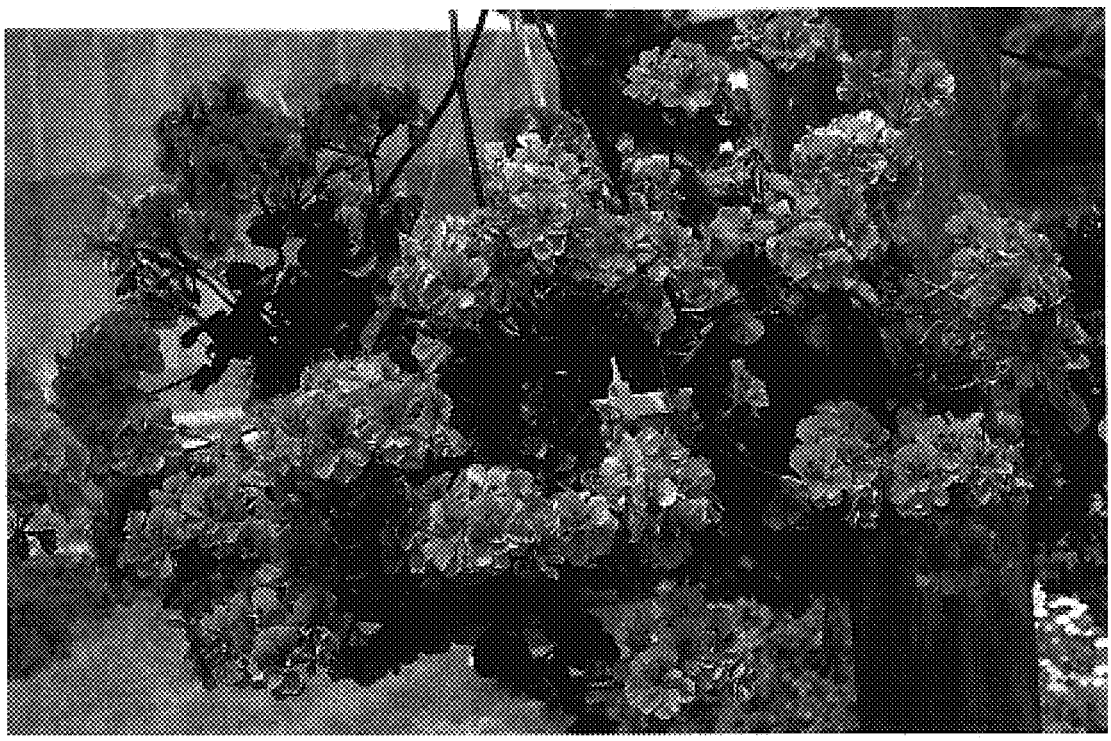

* * * * *